US009600883B2

United States Patent
Carlsen et al.

(10) Patent No.: US 9,600,883 B2
(45) Date of Patent: Mar. 21, 2017

(54) PLAUSIBLE REFERENCE CURVES FOR DYNAMIC, CONTRAST-ENHANCED IMAGING STUDIES

(75) Inventors: Ingwer C. Carlsen, Hamburg (DE); Kirsten Meetz, Hamburg (DE); Joerg Bredno, San Francisco, CA (US); Mark Olszewski, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1226 days.

(21) Appl. No.: 13/262,836

(22) PCT Filed: Mar. 9, 2010

(86) PCT No.: PCT/IB2010/051011
§ 371 (c)(1),
(2), (4) Date: Oct. 4, 2011

(87) PCT Pub. No.: WO2010/119355
PCT Pub. Date: Oct. 21, 2010

(65) Prior Publication Data
US 2012/0033869 A1    Feb. 9, 2012

Related U.S. Application Data

(60) Provisional application No. 61/168,655, filed on Apr. 13, 2009.

(51) Int. Cl.
*G06K 9/00* (2006.01)
*G06T 7/00* (2006.01)
(Continued)

(52) U.S. Cl.
CPC ...... *G06T 7/0016* (2013.01); *G01R 33/56366* (2013.01); *A61B 6/507* (2013.01);
(Continued)

(58) Field of Classification Search
USPC .................. 382/131, 128, 130, 132
See application file for complete search history.

(56) References Cited

U.S. PATENT DOCUMENTS 6,073,042 A    6/2000    Simonetti
6,377,835 B1   4/2002    Schoenberg et al.
(Continued)

FOREIGN PATENT DOCUMENTS

JP    01207038 A    8/1989
JP    2003210456 A    7/2003
(Continued)

OTHER PUBLICATIONS

Kim et al. "Automatic Registration of Postmortem Brain Slices to MRI Reference Volume", IEEE, 2000, pp. 1301-1303.*
(Continued)

*Primary Examiner* — Weiwen Yang (57) ABSTRACT

A comprehensive strategy is used to determine valid reference time-concentration curves (TCCs) from image data. The image data corresponds to a series of image scans acquired over time for an area of interest of a patient to which a contrast agent was previously administered. The image scans are initially registered to a common coordinate system. Then, observed potential reference TCCs in the image scans are compared to modeled reference TCCs to determine if the potential reference TCCs are plausible reference TCCs. Thereafter, any plausible reference TCCs are evaluated to determine if they contain residual, isolated motion artifacts. If a plausible reference TCC does not include any motion artifacts, the plausible reference TCC is considered a valid reference TCC. If a plausible reference TCC is determined to include motion artifacts, the plausible reference TCC is modified to a valid reference TCC by removing the motion artifacts, or otherwise the plausible (Continued)

reference TCC is rejected. The valid reference TCCs can be used to improve the effectiveness of dynamic, contrast-enhanced imaging studies.

24 Claims, 5 Drawing Sheets (51) Int. Cl.
*G01R 33/563* (2006.01)
*G01R 33/56* (2006.01)
*A61B 6/00* (2006.01)

(52) U.S. Cl.
CPC *G01R 33/5601* (2013.01); *G06T 2207/10081* (2013.01); *G06T 2207/10088* (2013.01); *G06T 2207/10104* (2013.01); *G06T 2207/10108* (2013.01); *G06T 2207/20108* (2013.01); *G06T 2207/30016* (2013.01); *G06T 2207/30104* (2013.01)

(56) References Cited

U.S. PATENT DOCUMENTS

| | | | |
|---|---|---|---|
| 6,512,807 | B1 | 1/2003 | Pohlman et al. |
| 2004/0117130 | A1* | 6/2004 | Denisov et al. ............... 702/20 |
| 2004/0218794 | A1 | 11/2004 | Kao et al. |
| 2007/0276225 | A1* | 11/2007 | Kaufman et al. ............ 600/416 |

FOREIGN PATENT DOCUMENTS

| | | |
|---|---|---|
| WO | 02086530 A1 | 10/2002 |
| WO | 03045245 A1 | 6/2003 |
| WO | 03046797 A2 | 6/2003 |
| WO | 2006086845 A1 | 8/2006 |
| WO | 2008034182 A1 | 3/2008 |

OTHER PUBLICATIONS

Collins et al. "Dynamic Magnetic Resonance Imaging of Tumor Perfusion", IEEE, 2004, pp. 65-83.*

Calamante, F., et al.; Defining a Local Arterial Input Function for Perfusion MRI Using Independent Component Analysis; 2004; MRM; 52:789-797.

Bader, T. R., et al.; Measurement of Hepatic Perfusion with Dynamic Computed Tomography: Assessment of Normal Values and Comparison of Two Methods to Compensate for Motion Artifacts; 2000; Investigative Radiology; 35(9)539-547.

Mlynash, M., et al.; Automated Method for Generating the Arterial Input Function on Perfusion-Weighted MR Imaging: Validation in Patients with Stroke; 2005; American Journal of Neuroradiology; 26(6)1480-1482.

Rogowska, J., et al.; Applications of Similarity Mapping in Dynamic MRI; 1995; IEEE Trans. on Medical Imaging; 14(3)480-486.

Sebastiani, G., et al.; Analysis of Dynamic Magnetic Resonance Images; 1996; IEEE Trans. on Medical Imaging; 15(3)253-277.

* cited by examiner

PLAUSIBLE REFERENCE CURVES FOR DYNAMIC, CONTRAST-ENHANCED IMAGING STUDIES

CROSS REFERENCE TO RELATED APPLICATIONS

This application claims the benefit of U.S. provisional application Ser. No. 61/168,655 filed Apr. 13, 2009, which is incorporated herein by reference.

The present application relates to medical imaging systems and methods for performing dynamic, contrast-enhanced imaging studies and, more particularly, to medical imaging systems and methods for determining plausible reference information for use in performing dynamic, contrast-enhanced imaging studies.

Functional imaging is a method of detecting or measuring changes in metabolism, blood flow, regional chemical composition, and absorption within a certain tissue or organ by using a medical imaging modality. Such medical imaging modalities include computed tomography (CT) systems, magnetic resonance (MR) systems, positron emission tomography systems (PET), and single photon emission computed tomography (SPECT) systems. A contrast agent is often used during functional imaging. A contrast agent is a substance used to enhance the contrast of structures or fluids within the body in medical imaging. In this manner, dynamic, contrast-enhanced studies are used in functional imaging, for example, to detect ischemia in the brain or blood perfusion and permeability in tumors. During such a study, images of the tissue of interest are repeatedly acquired during an acquisition time period to observe dynamics of the contrast agent over time.

Time-concentration curves TCC(t) of the contrast agent within tissues of interest can be analyzed to determine local blood volume, perfused blood flow, or the permeation rate of blood flow through compromised vessel walls. A quantitative analysis requires reference information to determine the dynamics of the contrast agent. Often, a timing reference and a volume reference are used to provide the reference information. A timing reference shows the dynamics of the contrast agent delivered to the tissue of interest, which is usually represented by an arterial input function AIF(t). A volume reference shows the amount of the contrast agent that passed through the tissue of interest, which is usually determined from a venous outflow function VOF(t).

Time-concentration curves, and especially reference curves AIF(t) and VOF(t), are only valid if they show the contrast agent concentration at an anatomically fixed point with no or minimal partial volume degradation. The results of a functional analysis from a dynamic study are heavily impacted by reference curves that are compromised by artifacts. Artifacts are misrepresentations of tissue structures seen in medical images. Artifacts can be caused, for example, by data acquisition errors, such as those resulting from motion during the imaging process. Since acquisition times are usually in the range of 45 seconds to a few minutes, motion artifacts become a major reason for quality degradation in the medical images. These motion artifacts can result from physiologic motion (e.g., the deformation of the liver over the respiratory cycle) and involuntary motion (e.g., head motion for a perfusion study in acute stroke, where patient compliance is difficult to obtain).

In view of the above, the general inventive concepts encompass a comprehensive approach to providing valid TCCs in the presence of artifacts, such as motion artifacts. Additionally, systems and methods for determining plausible reference curves for use in performing dynamic, contrast-enhanced imaging studies are disclosed.

An image processing system, according to one exemplary embodiment, can determine valid reference information such as time-concentration curves (TCCs) from image data. The image processing system includes a computer that receives the image data in the form of a series of image scans acquired over time, the image scans being of an area of interest of a patient to which a contrast agent was administered. The computer uses selection logic to process the image scans and automatically select locations at which observed reference information is compared to modeled reference information to obtain plausible reference information.

In one exemplary embodiment, the computer provides a graphical user interface (GUI) that displays the observed reference information and the modeled reference information. The GUI allows a user to review the comparison of the observed reference information and the modeled information, as well as interact therewith (e.g., change a scale of the displayed reference information).

The modeled reference information can be adjusted based on at least one of patient-specific, pathology-specific, and acquisition-specific information. For example, the modeled reference information can account for characteristics of the contrast agent, location of an injection site for the contrast agent, and the area of interest being imaged.

The image processing system, according to one exemplary embodiment, includes registration logic for registering the image scans to compensate for motion. The image scans include image data obtained by imaging a field of view (e.g., focused on the area of interest) over time to obtain first image data. This first image data is reconstructed to obtain a first dataset with a first slice thickness and a first slice distance (e.g., high resolution, thin slices). These thins slices can have a thickness, for example, of 1 to 2 mm.

The first dataset includes image data obtained from the same field of view. This image data is subject to patient motion. Accordingly, the first dataset is registered by the registration logic to compensate for motion in the first image data that occurred within the field of view. For example, the image scans are registered based on anatomical features in the area of interest that are not affected by the contrast agent.

Once registered, the first dataset can be used to form a second dataset with a second slice thickness and a second slice distance (e.g., thick slices). These thick slices can have a thickness, for example, of 5 to 10 mm. The functional analysis (e.g., a perfusion analysis) is performed on this second dataset. Furthermore, the selection logic (described below) can obtain the plausible reference information from either the first dataset or the second dataset.

Conversely, for a conventional perfusion analysis, only a single dataset and a single slice thickness (e.g., a thick slice) are typically utilized. In particular, registration is typically performed on thick slices, with thin slices not being reconstructed.

The image processing system, according to one exemplary embodiment, includes correction logic for determining if the plausible reference information includes motion artifacts. If the correction logic determines that the plausible reference information includes motion artifacts, the correction logic performs one of rejecting the plausible reference information and modifying the plausible reference information to account for the motion artifacts. Such correction may be achieved by using at least one of a valid portion of the observed reference information and knowledge from the modeled reference information.

A method, according to one exemplary embodiment, determines plausible reference information such as time-concentration curves (TCCs) from image data. The method includes acquiring the image data in the form of a series of image scans taken over a period of time, the image scans being of an area of interest of a patient to which a contrast agent was administered. The method also includes registering the image scans to a common coordinate system. According to the method, the image scans are processed to compare observed reference information from the image scans to modeled reference information to obtain plausible reference information. The method then confirms that the plausible reference information does not include a motion artifact. If the plausible reference information is determined to include a motion artifact, the plausible reference information is either modified using at least one of a valid portion of the observed reference information and knowledge from the modeled reference information, or otherwise rejected.

A computer program product, according to one exemplary embodiment, comprises a computer usable medium having a computer readable program code embodied therein, said computer readable program code adapted to be executed to implement a method of determining plausible reference information, such as time-concentration curves (TCCs), from image data in the form of a series of image scans taken over a period of time, the image scans being of an area of interest of a patient to which a contrast agent was administered. The method includes registering the image scans to a common coordinate system. According to the method, the image scans are processed to compare observed reference information from the image scans to modeled reference information to obtain plausible reference information. The method then confirms that the plausible reference information does not include a motion artifact. If the plausible reference information is determined to include a motion artifact, the plausible reference information is either modified using at least one of a valid portion of the observed reference information and knowledge from the modeled reference information, or otherwise rejected.

Still further advantages, features, and/or aspects of the general inventive concepts will become more readily apparent from the following detailed description of exemplary embodiments, from the claims and from the accompanying drawings. The invention may take form in various components and arrangements of components, and in various steps and arrangements of steps. The drawings are only for purposes of illustrating the exemplary embodiments disclosed herein, and are not to be construed as limiting the invention.

While the general inventive concepts are susceptible of embodiment in many different forms, there are shown in the drawings and will be described herein in detail specific embodiments thereof with the understanding that the present disclosure is to be considered as an exemplification of the principles of the general inventive concepts. Accordingly, the general inventive concepts are not intended to be limited to the specific embodiments illustrated herein.

Figure 1:
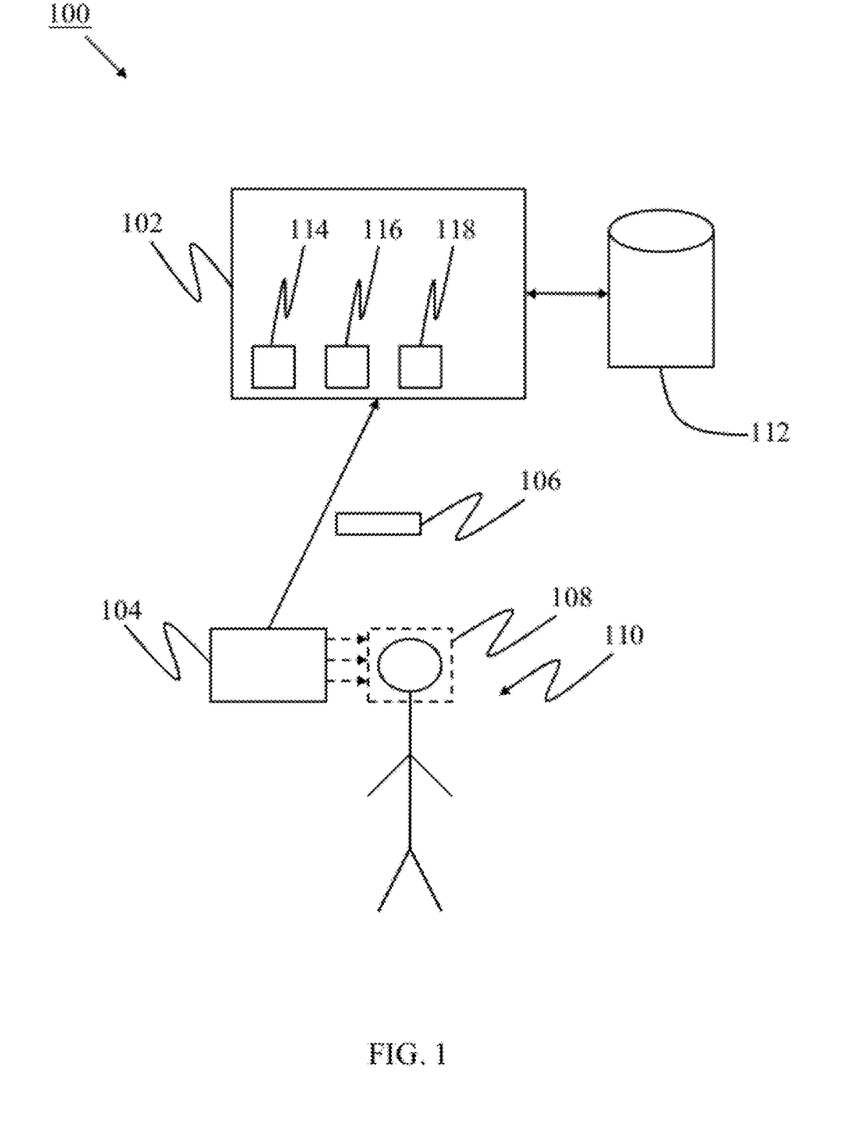
FIG. 1 is a system for determining plausible reference curves, according to one exemplary embodiment.

A system 100 for determining plausible reference curves for use in performing dynamic, contrast-enhanced imaging studies, according to one exemplary embodiment, is shown in FIG. 1. The system 100 includes one or more computer components. As used herein, "computer component" includes, but is not limited to, a computer-related entity, either hardware, firmware, software, a combination thereof, or software in execution. For example, a computer component can be, but is not limited to being, a processor, an object, an executable, a process running on a processor, a thread of execution, a program and a computer. By way of illustration, both an application running on a server computer and the server computer can be computer components. One or more computer components can reside within a process or thread of execution and a computer component can be localized on one computer or distributed between two or more computers. When "computer component" refers to a computer, it can also encompass various peripherals (e.g., input devices, data storage devices, display devices, and so on) for interfacing with the computer.

The system 100 can also include logic implemented by or interfaced with the computer components. As used herein, "logic" includes, but is not limited to, hardware, firmware, software or combinations of each to perform a function or an action, or to cause a function or action to be performed by another component. For example, based on a desired application or need, logic may include a software controlled microprocessor, discrete logic such as an application specific integrated circuit (ASIC), or other programmed logic device. Logic may also be fully embodied as software.

In the system 100, a computer component 102 is interfaced or otherwise in data communication with an image acquisition device or source 104 (e.g., corresponding to an imaging modality being used for the functional imaging). The image acquisition device 104 can be, for example, a CT scanner. The image acquisition device 104 is able to acquire image data 106 for multiple images (e.g., slices) of an area of interest 108 of a patient 110 over time. Prior to or during acquisition of the image data 106 by the image acquisition device 104, a contrast agent (not shown) may be administered to the patient 110 for delivery (e.g., via the patient's circulatory system) to the area of interest 108.

The computer component 102 is also interfaced or otherwise in data communication with a data storage device 112. The computer component 102 can store data to and retrieve data from the data storage device 112.

The computer component 102 includes, or is interfaced or otherwise in data communication with, registration logic 114, selection logic 116, and correction logic 118. The registration logic 114 registers volumes of the image data 106 acquired over time to a common coordinate system. The registration process can be adapted according to specific requirements of the subsequent functional analysis. The selection logic 116 automatically selects plausible locations within the image data 106 for determining reference information, for example reference curves such as reference TCCs. The selection process may be based on how closely such imaging data from locations match a modeled expectation of plausible reference information. The modeled expectation can be adjusted based on patient-specific, pathology-specific, and/or acquisition-specific information. Thereafter, the correction logic 118 modifies or rejects individual samples within the group of selected plausible reference curves that remain compromised, for example by motion artifacts. The registration logic 114, the selection logic 116, and/or the correction logic 118 can be implemented as separate logic or integrated logic.

The image data 106 generated from scanning a field of view (e.g., focused on the area of interest) over time is used to generate a first dataset comprising a series of relatively thin (e.g. 1 to 2 mm) image "slices." This first dataset is then registered by the registration logic 114 to compensate for motion artifacts in the image data 106. Once registered, the first dataset is used to form a second dataset comprising relatively thick (e.g. 5to 10 mm) slices, formed by combining several of the registered thin slices. The registration logic 114 registers the thin slices, prior to using the thin slices to form the thicker slices, in order to avoid or otherwise reduce mixing and smearing of features such as arterial networks in the scans that would otherwise result from motion artifacts in the thin slices. The thicker slices can then be used for the functional analysis (e.g., a perfusion analysis). The thicker slices, for example, reduce the otherwise large amount of data and boost the signal-to-noise level of contrast agent in regions with low perfusion values.

As noted above, the computer component 102 can receive a series of scans (i.e., the image data 106) acquired over time by the image acquisition device 104. The scans are of the area of interest 108 of the patient 110, such as the brain, the liver or portions thereof. Because the scans are acquired at different times, the scans comprising the image data 106 may show the object of interest and its motion in the field of view. Accordingly, registration of the image data 106 transforms the different scans so that this motion is compensated.

The registration of the scans can be challenging because of changes in the image data 106 over time, namely, due to the arrival, inflow, and washout of the attenuating contrast agent, and a slice thickness optimized for a perfusion analysis. In general, the registration logic 114 implements a registration process or algorithm adapted to this task. In this manner, the computer component 102 uses the registration logic 114 to register the image data 106 for the dynamic, contrast-enhanced image study.

The registration process may be based on available anatomical features in the area of interest 108 (and, thus, in the image data 106) that are not affected by arrival of the contrast agent. For example, in a brain perfusion scan, the skull could be segmented first. The skull could then serve as an input to the registration process, whereas the attenuating brain tissue would not be taken into account during the registration process.

In some cases, however, the area of interest 108 does not provide sufficient image data 106 that is unaffected by the contrast agent. One example is perfusion scans of the liver. In such cases, the registration process can use a similarity measure that can robustly handle changes in global and local attenuation over time. The mutual information of image data at two time points or the entropy of the histogram of the difference image of image data at two time points are examples of similarity measures that could be used in the registration process.

Next, the computer component 102 can use the selection logic 116 to read TCCs from any position in the image data 106 (e.g., the first dataset or the second dataset). However, only a few of the positions are likely suitable for providing plausible reference TCCs, perhaps even an individual voxel in the data. Thus, the selection logic 116 implements an automated selection process or algorithm that ensures the plausibility of reference curves in the presence of motion artifacts and other image quality issues.

Figure 2A:
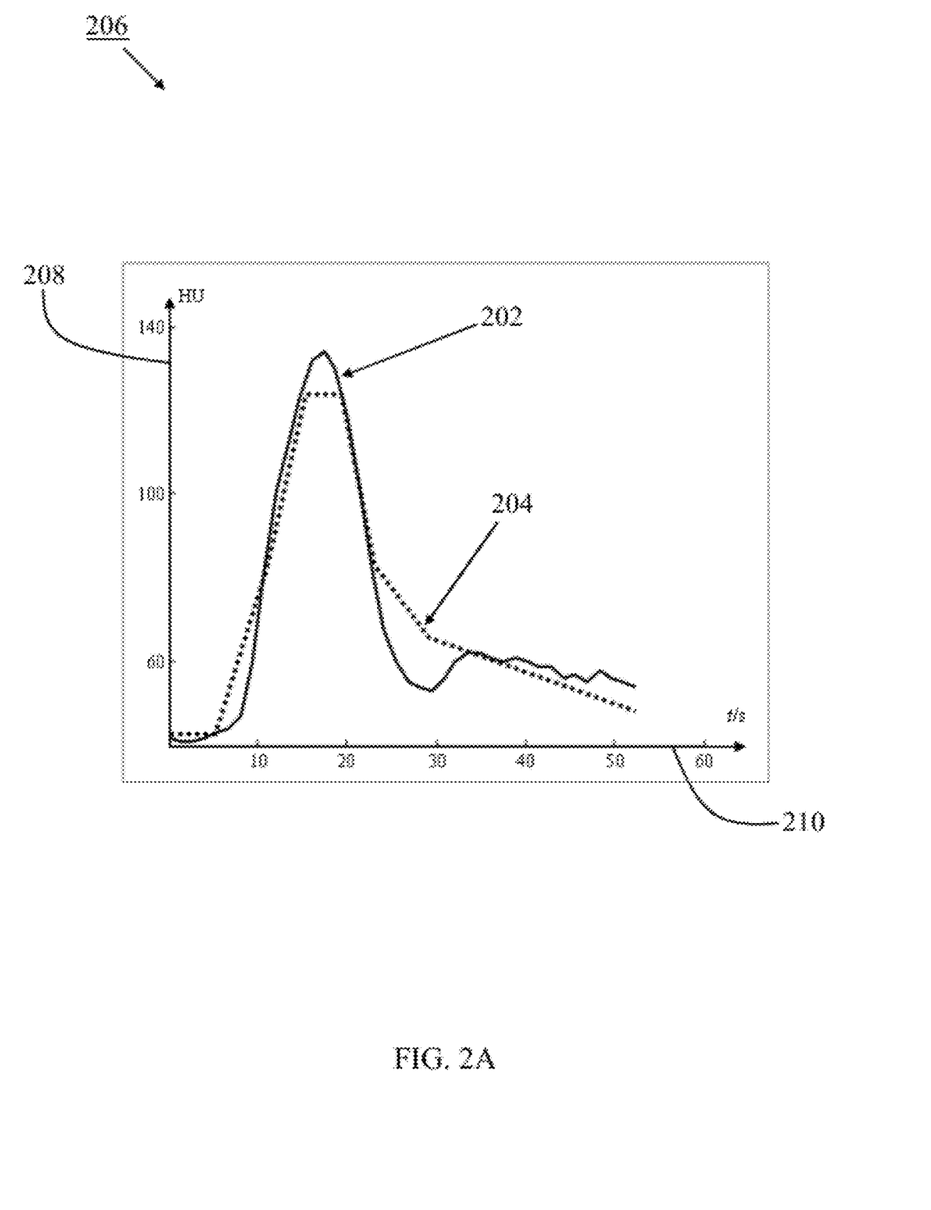
FIG. 2A is a graph showing an arterial TCC, according to one exemplary embodiment, wherein an observed curve (solid line) is shown together with a fitted model curve (dotted line).
Figure 2B:
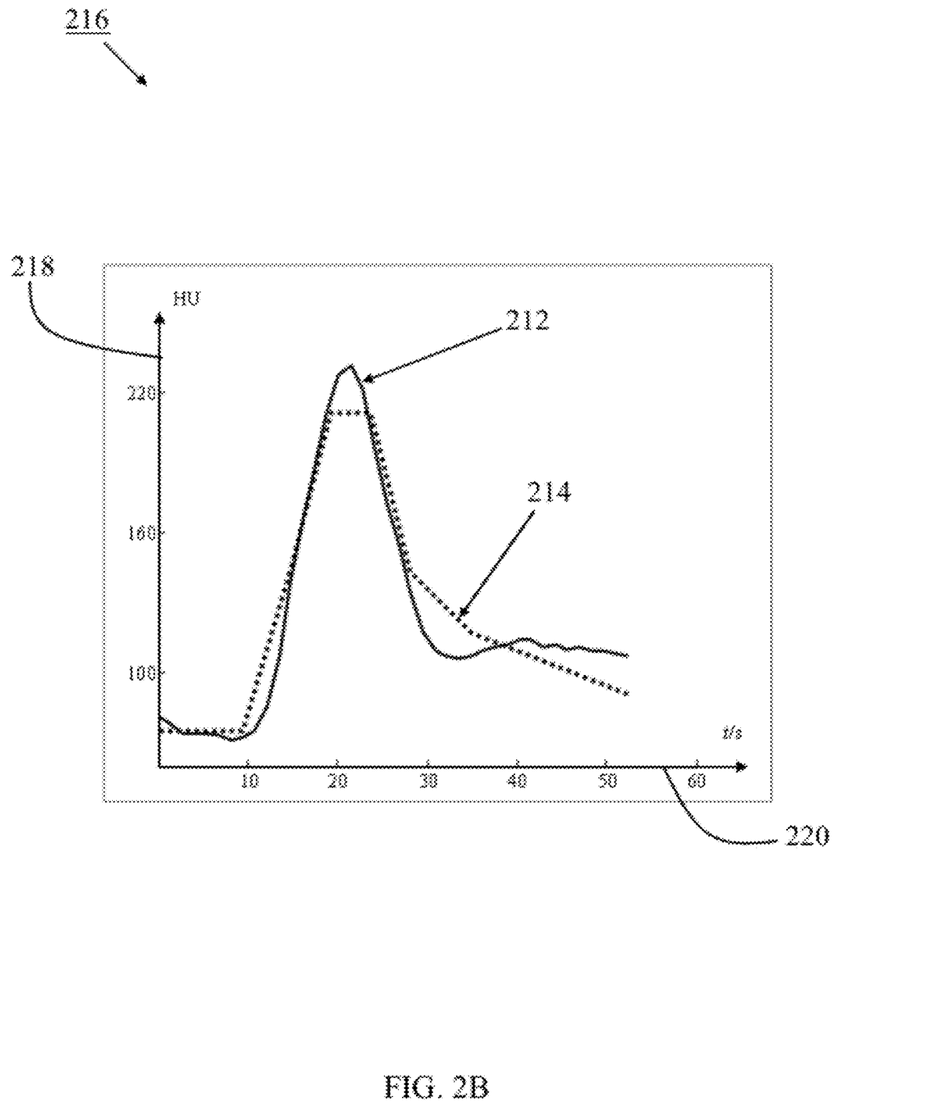
FIG. 2B is a graph showing a venous TCC, according to one exemplary embodiment, wherein an observed curve (solid line) is shown together with a fitted model curve (dotted line).

The selection logic 116 determines the plausibility of an observed curve in the image data 106 based on its similarity to an ideal or otherwise model curve. For example, as shown in FIGS. 2A and 2B, the plausibility of an observed TCC 202 or 212 in the image data 106 may be determined based on its similarity to a model TCC 204 or 214. Individual model curves can be generated based on the best possible fit to observations. In one exemplary embodiment, the model curves are further adjusted to additional, external information. In this manner, the model curves can be further fine tuned using image-based and/or non-image-based information.

As noted above, the computer component 102 can include a GUI for displaying the observed TCC (e.g., TCC 202 or 212) and the model TCC (e.g., TCC 204 or 214). In this manner, a user can review the observed TCC and the model TCC to which it is being compared. Furthermore, the GUI can allow the user to interact with the observed TCC and/or the model TCC.

By way of example, the automated selection process will be described in the context of a model-based detection of a reference artery and vein for brain perfusion analysis. A model curve such as 204 or 214, according to one exemplary embodiment, is defined based on the following expected characteristics of a plausible TCC: (1) no attenuation is observed before the arrival of the main bolus of the contrast agent; (2) the curve rises monotonously to its peak; (3) the curve decays initially with a similar rate as that on the raising flank (symmetric main bolus); and (4) the curve then decays slowly back to nearly the initial baseline (dispersion of the contrast agent). One of ordinary skill in the art will appreciate that fewer than or more than these characteristics, as well as different characteristics, could be used to define the model curve.

In one exemplary embodiment, individual model curves are generated by the detection of bolus arrival time (BAT), half-peak arrival time (HPAT), half-peak decay time (HPDT), time to peak (TTP), and the final baseline elevation for the particular contrast agent, injection site, and area of interest 108. These values are modified, according for example to the measures noted above (e.g., BAT, HPAT, HPDT, TTP, and final baseline elevation, as quantitative features extracted for an observed curve), to promote symmetry, decay back down to baseline, etc. In general, the measures are any quantitative features of a curve and the respective modifications thereto that make the curve more symmetric, let it decay down closer to the baseline, or let the time points and observed concentration values better reflect desired and expected features.

A comparison between the fitted model curve and the observed curve from the image data 106 provides a quality measure as a ratio of the area under a difference curve (i.e., the disagreement between model and observation) and the area under the observed curve. One of ordinary skill in the art will appreciate that this ratio is just an example and any other quality measure reflecting a satisfactory match between curves could be used. Using the quality measure, vessels that provide plausible reference curves are detected.

For example, as seen in FIG. 2A, an artery is evaluated to determine whether it provides a plausible reference TCC by comparing an observed curve 202 to an appropriate model curve 204. For purposes of illustration, the observed curve 202 (solid line) and the model curve 204 (dotted line) are shown plotted on a graph 206 having a y-axis 208 representing Hounsfield units and an x-axis 210 representing time (in seconds). If the computer component 102 (using the selection logic 116) determines that the observed curve 202 sufficiently conforms to the model curve 204, based on a predefined similarity or quality metric, then the observed curve 202 (corresponding to the artery) is selected as a plausible reference TCC.

Similarly, as seen in FIG. 2B, a vein is evaluated to determine whether it provides a plausible reference TCC by comparing an observed curve 212 to an appropriate model curve 214. For purposes of illustration, the observed curve 212 (solid line) and the model curve 214 (dotted line) are shown plotted on a graph 216 having a y-axis 218 representing Hounsfield units and an x-axis 220 representing time (in seconds). If the computer component 102 (using the selection logic 116) determines that the observed curve 212 sufficiently conforms to the model curve 214, based on a predefined similarity or quality metric, then the observed curve 212 (corresponding to the vein) is selected as a plausible reference TCC.

Figure 3:
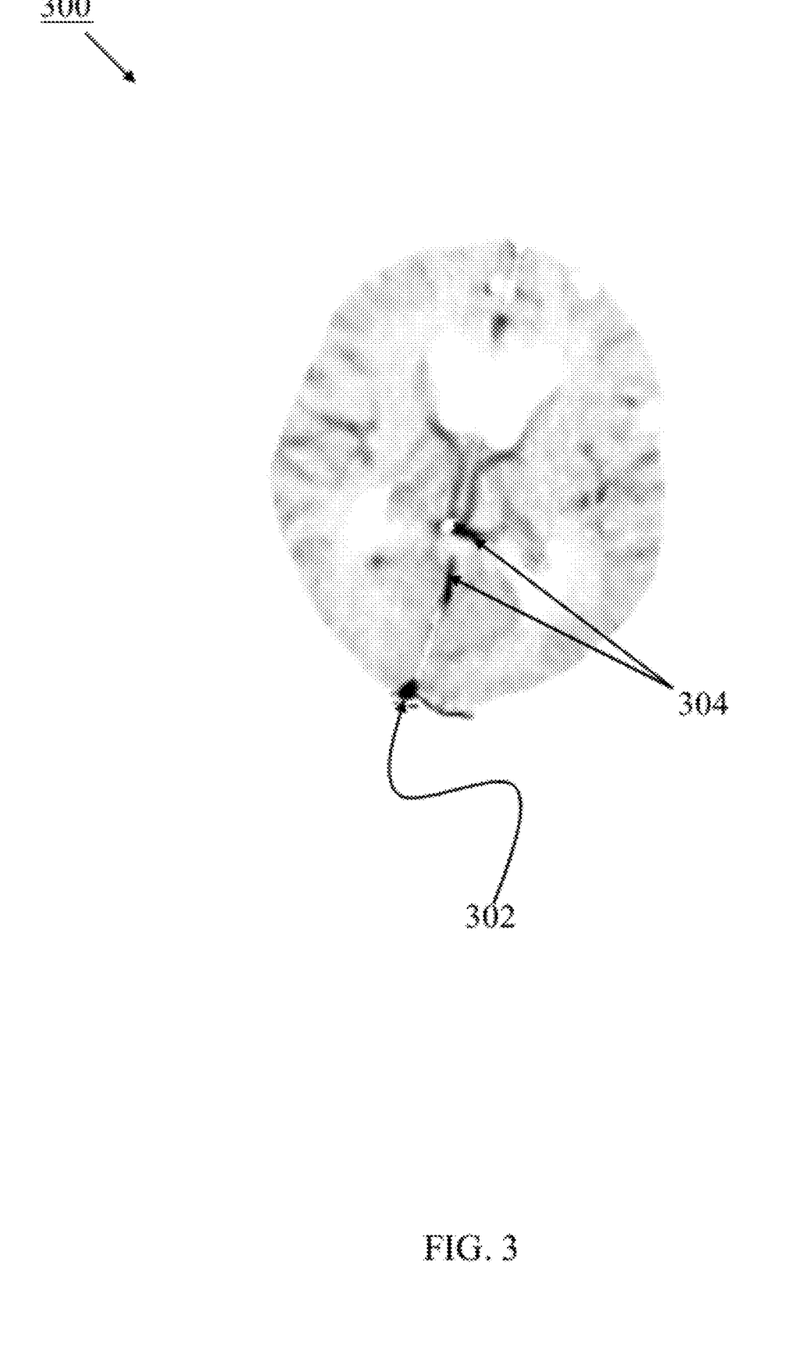
FIG. 3 is an image of a transverse slice of a brain, according to one exemplary embodiment, wherein a quality criterion based on the similarity between modeled and observed results is used to automatically find a reference vein for a brain perfusion application.

A reference vein for a brain perfusion application can be determined by using a predefined similarity or quality metric, according to one exemplary embodiment, which is based on a determination of the similarity between an observed curve such as 202 or 212 and a modeled curve such as 204 or 214, as well as the area under the observed curve (i.e., the amount of the contrast agent). Certain voxels, which appear as dark voxels in a processed slice of image data 106, receive the highest values as a result of application of the similarity or quality metric. As shown in FIG. 3, a slice 300 includes voxels in the superior sagittal sinus and Vein of Galen regions that received the highest values and, thus, appear dark in the image. For example, the dark dot 302 represents a vessel extending through (i.e., oriented perpendicular to) the slice 300, while the dark lines 304 represent vessels extending along (i.e., oriented in line with) the slice 300. One or more of these vessels could be considered a candidate plausible reference vessel.

In the selection process, a modeled curve such as 204 or 214 and an observed curve such as 202 or 212 only match if the defined expectations, such as those given above, are actually met. For curves with an arbitrary shape, the detected characteristics (e.g., BAT, HPAT, HPDT, TTP) cannot be used to generate a valid model that is similar to the observation. Consequently, a set of different criteria are used to further describe expected curves for the contrast agent, injection site, and area of interest 108. As noted above, the model can also be adjusted, for example, based on externally available, non-image information. Such non-image information may include, for example, the contrast agent injector settings like the concentration and total amount of contrast agent, the duration of injection, the delay from injection to the start of image acquisition, and the like. The non-image information may also include basic information on the patient's cardiac status, like a heart rate, blood pressure, or cardiac output. This additional information can be used to define expected arrival times of the contrast agent and peak enhancements in an AIF. If a perfusion scan is acquired after previous injections of the contrast agent (e.g., following a CTA or a timing test scan), then the dynamics of the contrast agent observed in these prior scans can further drive the reference vessel detection.

An adaptive registration process and an intelligent reference selection process, such as those described above, should result in the best available reference curves being selected. However, even the reference curves resulting from these processes may still exhibit motion artifacts. For example, strong motion from coughing can result in unusable frames in brain and/or liver perfusion scans.

Thus the correction logic 118 implements a correction process or algorithm for detecting residual, isolated motion artifacts in the candidate reference TCCs. These motion artifacts can be detected, for example, by a detailed analysis of the goodness measure used in the registration process, or by a comparison of the measured reference curves to their best fitting model representation. The TCC samples having isolated motion artifacts can be easily corrected for those artifacts by an interpolation across the affected portion of the curve, using the valid parts of the observed curve and/or knowledge from the model curves. When all of the image data 106 and not only the candidate reference TCCs are affected by an isolated motion artifact, then all of the image data 106 at the affected time points can either be removed from analysis or replaced with a reasonable, interpolated approximation.

In one exemplary embodiment, the correction process includes local motion compensation. For time points corrupted by motion, a local registration can be performed in the neighborhood of reference vessels to ensure the extraction of a plausible reference TCC from a fixed anatomical structure.

In one exemplary embodiment, the computer component 102 is integrated or otherwise interfaced with the image acquisition device 104 to form a scanner console. The registration process, the selection process, and/or the correction process are all executed at the same scanner console (e.g., to save time in the acute setting). In other exemplary embodiments, the computer component 102 is a clinical workstation or a network client computer connected to a network server or clinical workstation running, for example, a perfusion analysis. The registration process, the selection process, and/or the correction process are executed at the workstation or thin client. In yet another exemplary embodiment, the registration process, the selection process, and/or the correction process utilize distributed network systems, such as picture archiving and communication systems (PACS).

Figure 4:
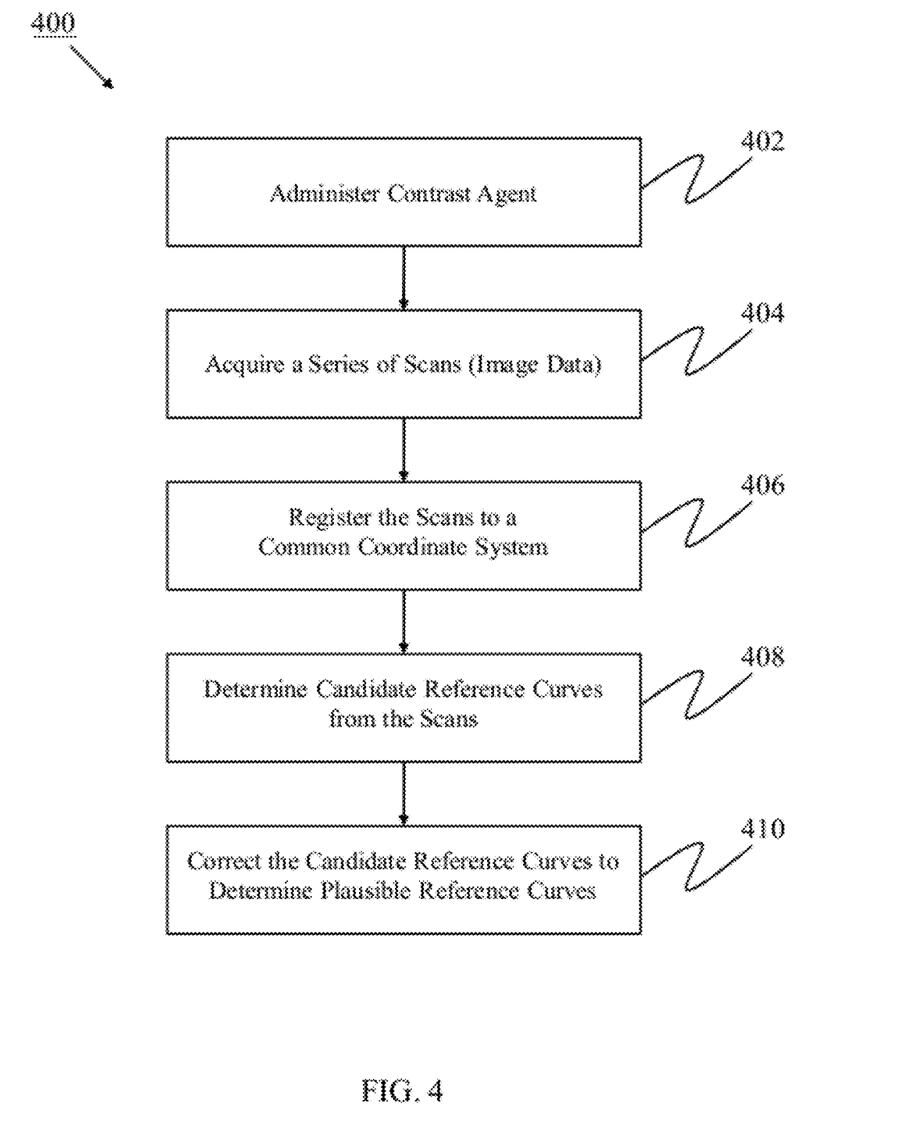
FIG. 4 is a method of determining plausible reference curves, according to one exemplary embodiment.

A method 400 of determining plausible reference curves for use in performing dynamic, contrast-enhanced imaging studies, according to one exemplary embodiment, is shown in FIG. 4. As an initial step 402, a contrast agent is administered to a patient for delivery to an area of interest, such as the brain or liver. The delivery often involves transport of the contrast agent to the area of interest through the patient's circulatory system. Then, in step 404, the method 400 includes acquiring a series of images (e.g., image data) of the area of interest spanning a period of time, i.e., the acquisition time. During the imaging data acquisition, the contrast agent is flowing through the area of interest in the patient's bloodstream.

Because the scans are acquired at different times, the scans representing the acquired image data may show the object of interest and its motion in the field of view. As noted above, the image data is initially reconstructed to obtain a first dataset with a first slice thickness and a first slice distance (e.g., high resolution, thin slices). These thins slices can have a thickness, for example, of 1 to 2 mm. The first dataset includes image data obtained from the same field of view and which is subject to patient motion. Accordingly, in step 406, the first dataset is registered to compensate for motion that occurred within the field of view. For example, the image scans are registered based on anatomical features in the area of interest that are not affected by the contrast agent.

Once registered, the first dataset can be used to form a second dataset with a second slice thickness and a second slice distance (e.g., thick slices). These thick slices can have a thickness, for example, of 5 to 10 mm. The thick slices are well suited for the functional analysis (e.g., a perfusion analysis).

In step 408, the scans (e.g., the first dataset or the second dataset) are processed to determine candidate reference information (e.g., curves such as TCCs). This determination measures the plausibility of reference curves in the presence of motion artifacts and other image quality issues. In particular, the scans are processed to determine the plausibility of an observed curve based on its similarity to an ideal or otherwise model curve, such as shown for example in FIGS. 2A and 2B. Individual model curves can be generated based on the best possible fit to observations. In one exemplary embodiment, the model curves are further adjusted to additional, external information. In this manner, the model curves can be further fine tuned using image-based and/or non-image-based information.

As noted above, a model curve, according to one exemplary embodiment, is defined based on the following expected characteristics of a plausible TCC: (1) no attenuation is observed before the arrival of the main bolus of the contrast agent; (2) the curve rises monotonously to its peak; (3) the curve decays initially with a similar rate as that on the raising flank (symmetric main bolus); and (4) the curve then decays slowly back to nearly the initial baseline (dispersion of the contrast agent). One of ordinary skill in the art will appreciate that fewer than or more than these characteristics, as well as different characteristics, could be used to define the model curve.

In one exemplary embodiment, individual model curves are generated by the detection of bolus arrival time (BAT), half-peak arrival time (HPAT), half-peak decay time (HPDT), time to peak (TTP), and the final baseline elevation for the particular contrast agent, injection site, and area of interest. These values are modified, according for example to the measures noted above, to promote symmetry, decay back down to baseline, etc. In general, the measures are any quantitative features of a curve and the respective modifications thereto that make the curve more symmetric, let it decay down closer to the baseline, or let the time points and observed concentration values better reflect desired and expected features.

A comparison between the fitted model curve and the observed curve provides a quality measure as a ratio of the area under a difference curve (i.e., the disagreement between model and observation) and the area under the observed curve. One of ordinary skill in the art will appreciate that this ratio is just an example and any other quality measure reflecting a satisfactory match between curves could be used. Using the quality measure, vessels that provide plausible reference curves are detected.

In step 408, a modeled curve and an observed curve only match if the defined expectations, such as those given above, are actually met. For curves with an arbitrary shape, the detected characteristics (e.g., BAT, HPAT, HPDT, TTP) cannot be used to generate a valid model that is similar to the observation. Consequently, a set of different criteria are used to further describe expected curves for the contrast agent, injection site, and area of interest. As noted above, the model can also be adjusted, for example, based on externally available, non-image information, such as the injector settings or basic information on the patient's cardiac status. This additional information can be used to define expected arrival times of the contrast agent and peak enhancements in an AIF. If a perfusion scan is acquired after previous injections of the contrast agent (e.g., following a CTA or a timing test scan), then the dynamics of the contrast agent observed in these prior scans can further drive the reference vessel detection.

Once the scans are processed to determine a set comprising one or more candidate plausible reference curves, some of the candidate reference curves may still exhibit motion artifacts (e.g., strong motion from coughing can result in unusable frames in brain and/or liver perfusion scans). Consequently, the set of candidate plausible reference curves is corrected, in step 410, to form a set comprising one or more plausible reference curves.

This correction involves detecting residual, isolated motion artifacts in the candidate reference TCCs. These motion artifacts can be detected, for example, by a detailed analysis of the goodness measure used in the registration process, or by a comparison of the measured reference curves to their best fitting model representation. The candidate TCCs having isolated motion artifacts can be easily corrected for those artifacts by an interpolation across the affected portion of the curve, using the valid parts of the observed curve and/or knowledge from the model curves. When all of the scans of image data and not only the candidate reference TCCs are affected by an isolated motion artifact, then all of the image data 106 at the affected time points can either be removed from analysis or replaced with a reasonable, interpolated sample.

In one exemplary embodiment, the refinement or correction in step 410 includes local motion compensation. For time points corrupted by motion, a local registration can be performed in the neighborhood of reference vessels to ensure the extraction of a plausible reference TCC from a fixed anatomical structure. As a result of the refinement in step 410, the set of plausible reference TCCs is obtained and can be used in the dynamic, contrast-enhanced imaging studies.

As noted above, as part of the method 400, the registration 406, selection 408 and/or the correction 410 may be performed on relatively thin image slices (e.g. 1 to 2 mm) before they are subsequently reformatted into thicker (e.g., 5 to 10 mm) slices for use in imaging studies.

In view of the above, the exemplary system 100 and the exemplary method 400 illustrate how the general inventive concepts can be used to provide a comprehensive strategy for providing valid reference TCCs, which can be used to improve the effectiveness of dynamic, contrast-enhanced studies.

The above description of specific embodiments has been given by way of example. From the disclosure given, those skilled in the art will not only understand the general inventive concepts and any attendant advantages, but will also find apparent various changes and modifications to the structures and methods disclosed. It is sought, therefore, to cover all such changes and modifications as fall within the spirit and scope of the general inventive concepts, as defined by the appended claims, and equivalents thereof.

What is claimed is:

1. An image processing system, the system comprising:
   a computer,
   wherein the computer receives a plurality of image scans acquired over time, the image scans being of an area of interest of a patient to which a contrast agent was administered;

wherein the computer uses registration logic to register the image scans to a common coordinate system to compensate for artifacts in the image scans;

wherein the computer uses selection logic to process the image scans and automatically select locations at which observed reference information is compared to modeled reference information to obtain plausible reference information;

wherein the observed reference information includes a time-concentration curve representing an observed curve and the modeled reference information includes a time-concentration curve representing a model curve.

2. The system of claim 1, wherein the modeled reference information is adjusted based on at least one of patient-specific, pathology-specific, and acquisition-specific information.

3. The system of claim 1, wherein the computer uses registration logic to register a first image dataset comprising a first plurality of images having a first slice thickness to the common coordinate system, and then to form a second image dataset comprising a second plurality of images having a second slice thickness, and wherein the image scans comprises at least one of the first image dataset and the second image dataset.

4. The system of claim 1, wherein the model curve has characteristics including (a) no attenuation is observed before the arrival of a main bolus of the contrast agent; (b) the model curve rises monotonously from a baseline to its peak; the model curve decays initially at a rate similar to a rate at which the model curve rose; and the model curve then decays slowly back to near the baseline as the contrast agent disperses.

5. The system of claim 1, wherein the model curve is generated by detecting at least one of a bolus arrival time, a half-peak arrival time, a half-peak decay time, a time to peak, and a final baseline elevation for the contrast agent.

6. The system of claim 1, wherein the model curve accounts for characteristics of the contrast agent, location of an injection site for the contrast agent, and the area of interest of the patient.

7. The system of claim 1, wherein the model curve is adjusted based on non-image information.

8. The system of claim 7, wherein the non-image information is information regarding the patient.

9. The system of claim 1, wherein the selection logic measures a similarity between the observed curve and the corresponding model curve.

10. The system of claim 9, wherein the selection logic determines a similarity measure as a ratio of an area under a difference curve, which corresponds to an amount of disagreement between the observed curve and the model curve, to an area under the observed curve.

11. The system of claim 3, wherein the computer uses registration logic to compensate for motion in the first image dataset.

12. The system of claim 11, wherein the first image dataset is registered based on at least one anatomical feature in the area of interest that is not affected by the contrast agent.

13. The system of claim 11, wherein the first slice thickness is less than the second slice thickness.

14. The system of claim 13, wherein the first slice thickness is 1 to 2 mm; and wherein the second slice thickness is 5 to 10 mm.

15. The system of claim 1, wherein the computer uses correction logic to determine if the plausible reference information includes motion artifacts, and if the plausible reference information is determined to include motion artifacts, the correction logic performs one of rejecting the plausible reference information and modifying the plausible reference information.

16. The system of claim 1, further comprising an image acquisition device, wherein the computer is interfaced with the image acquisition device, and wherein the computer receives the image scans from the image acquisition device.

17. The system of claim 16, wherein the computer and the image acquisition device are integrated into a console scanner.

18. The system of claim 11, wherein the registration logic, the selection logic, and the correction logic are integrated.

19. The system of claim 1, wherein the computer includes a graphical user interface for displaying the observed reference information and the modeled reference information at the same time.

20. The system of claim 19, wherein the graphical user interface allows a user to interact with at least one of the observed reference information and the modeled reference information.

21. A method of determining plausible reference information from image data, the method comprising:

acquiring the image data in the form of a series of image scans taken over a period of time, the image scans being of an area of interest of a patient to which a contrast agent was administered;

registering the image scans to a common coordinate system to compensate for artifacts in the image scans;

automatically selecting locations at which observed reference information is compared to modeled reference information;

processing the image scans to compare observed reference information from the image scans to modeled reference information at the selected locations to obtain plausible reference information, wherein the observed reference information includes a time-concentration curve representing an observed curve and the modeled reference information includes a time-concentration curve representing a model curve; and confirming the plausible reference information does not include a motion artifact.

22. The method of claim 21, further comprising, if the plausible reference information is determined to include a motion artifact, performing one of rejecting the plausible reference information and modifying the plausible reference information.

23. A computer program product, comprising a computer usable non-transitory medium having a computer readable program code embodied therein, said computer readable program code adapted to be executed to implement a method of determining plausible reference information from image data in the form of a series of image scans taken over a period of time, the image scans being of an area of interest of a patient to which a contrast agent was administered, the method comprising:

registering the image scans to a common coordinate system to compensate for artifacts in the image scans;

automatically selecting locations at which observed reference information is compared to modeled reference information;

processing the image scans to compare observed reference information from the image scans to modeled reference information at the selected locations to obtain plausible reference information, wherein the observed reference information includes a time-concentration curve representing an observed curve and the modeled reference information includes a time-concentration curve representing a model curve; and confirming the plausible reference information does not include a motion artifact.

24. The computer program product of claim 23, wherein the method further comprises, if the plausible reference information is determined to include a motion artifact, performing one of rejecting the plausible reference information and modifying the plausible reference information.

* * * * *